(12) United States Patent
Prade et al.

(10) Patent No.: US 12,064,212 B2
(45) Date of Patent: Aug. 20, 2024

(54) DEVICE AND METHOD FOR OPTOACOUSTIC SENSING

(71) Applicant: Helmholtz Zentrum München Deutsches Forschungszentrum Für Gesundheit und Umwelt (GMBH), Neuherberg (DE)

(72) Inventors: Ludwig Prade, Edinburgh (GB); Vasilis Ntziachristos, Munich (DE)

(73) Assignee: Helmholtz Zentrum Munchen Deutsches Forschungszentrum Fur Gesundheit und Umwelt (GMBH), Neuherberg (DE)

( * ) Notice: Subject to any disclaimer, the term of this patent is extended or adjusted under 35 U.S.C. 154(b) by 81 days.

(21) Appl. No.: 16/629,490

(22) PCT Filed: Jul. 10, 2018

(86) PCT No.: PCT/EP2018/068702
§ 371 (c)(1),
(2) Date: Jan. 8, 2020

(87) PCT Pub. No.: WO2019/011933
PCT Pub. Date: Jan. 17, 2019

(65) Prior Publication Data
US 2021/0137390 A1 May 13, 2021

(30) Foreign Application Priority Data
Jul. 10, 2017 (EP) ..................................... 17180450

(51) Int. Cl.
*A61B 5/00* (2006.01)
*A61B 8/08* (2006.01)

(52) U.S. Cl.
CPC .......... *A61B 5/0095* (2013.01); *A61B 5/7203* (2013.01); *A61B 5/7228* (2013.01); *A61B 8/5207* (2013.01)

(58) Field of Classification Search
CPC ... A61B 5/0095; A61B 5/7203; A61B 5/7228; A61B 8/5207
See application file for complete search history.

(56) References Cited

U.S. PATENT DOCUMENTS

| | | | |
|---|---|---|---|
| 6,846,288 B2* | 1/2005 | Nagar | A61B 5/1455 600/316 |
| 9,330,452 B2* | 5/2016 | Zalev | A61B 5/004 |

(Continued)

OTHER PUBLICATIONS

Press et a. (2007). Numerical Recipes in C: The Art of Scientific Computing (3rd Edition). United Kingdom: Cambridge University Press. (pp. 605-606) (Year: 2007).*

(Continued)

*Primary Examiner* — Patricia J Park
(74) *Attorney, Agent, or Firm* — Dorsey & Whitney LLP (57) ABSTRACT

The invention relates to a device and a method for optoacoustic sensing, wherein an irradiation unit is configured to generate at least one train of periodic pulses of electromagnetic energy, the pulses of the at least one train of periodic pulses exhibiting a pulse duration and repetition rate, and to irradiate a target with the generated train of periodic pulses. A detection unit is configured to detect acoustic waves generated in the target and to generate an according detection signal, the detection signal comprising, for each train of the at least one train of periodic pulses, detection signal components at a plurality of discrete frequencies in the frequency domain, the discrete frequencies being spaced from each other by a frequency spacing corresponding to the repetition rate of the pulses of the at least one train of periodic pulses. Further, a processing unit is configured to (Continued)

modify the detection signal in the frequency domain to obtain a modified detection signal, and to derive at least one property of the target based on the modified detection signal.

18 Claims, 6 Drawing Sheets

(56) References Cited

U.S. PATENT DOCUMENTS

| | | |
|---|---|---|
| 2005/0150309 A1 | 7/2005 | Beard |
| 2009/0221900 A1* | 9/2009 | Ikushima ............ A61B 5/4064 600/409 |
| 2013/0102865 A1 | 4/2013 | Mandelis et al. |
| 2014/0175261 A1* | 6/2014 | Addison ............ A61B 5/02416 250/206 |
| 2015/0238091 A1* | 8/2015 | Iyer ...................... A61B 5/0095 600/407 |
| 2016/0313233 A1 | 10/2016 | Zangmeister et al. |
| 2017/0223788 A1* | 8/2017 | Jamsa ................ H05B 45/3725 |

OTHER PUBLICATIONS

Minamikawa et al. "Optical-frequency-comb based ultrasound sensor," Proc. SPIE 10064, Photons Plus Ultrasound: Imaging and Sensing 2017, 100645C (Mar. 3, 2017); https://doi.org/10.1117/12.2250792 (Year: 2017).*

Shi, et al., Photoacoustic Imaging Using Lock-In Amplification and Pulsed Fiber Lasers, Progress in Biomedical Optics and Imaging, SPIE—International Society for Optical Engineering, vol. 9708, Mar. 15, 2016, 970841.

* cited by examiner

DEVICE AND METHOD FOR OPTOACOUSTIC SENSING

This patent application is a U.S. National Stage filing under 35 U.S.C. 371 of International Patent Application No. PCT/EP2018/068702 entitled "DEVICE AND METHOD FOR OPTOACOUSTIC SENSING," filed Jul. 10, 2018, which claims priority to European Patent Application No. 17180450.3, filed Jul. 10, 2017, each of which is incorporated herein by reference in its entirety.

DESCRIPTION

The present invention relates to a device and a method for optoacoustic sensing, in particular optoacoustic imaging, according to the independent claims.

Optoacoustic signal generation is based on the photoacoustic effect, according to which ultrasonic waves are generated due to absorption of electromagnetic radiation by an object, e.g. a biological tissue, and a subsequent thermoelastic expansion of the object. Excitation radiation, for example laser light or radiofrequency radiation, can be pulsed radiation or continuous radiation with varying amplitude or frequency.

Optoacoustic imaging in the frequency domain (FD) allows for simultaneous multi-wavelength imaging. However, although implementations of FD systems capturing amplitude and phase of ultrasound waves stimulated by light exhibiting a sinusoidal intensity modulation have been proposed as economic alternatives to time-domain (TD) systems, FD systems usually fail to yield the signal-to-noise ratio (SNR) achieved by TD approaches. In addition, in FD optoacoustic imaging the requirement to scan multiple modulation frequencies slows down data acquisition.

It is an object of the invention to provide a device and method for fast and economic optoacoustic sensing, in particular optoacoustic imaging, with enhanced signal-to-noise ratio.

The object is achieved by a device and method according to the independent claims.

The device according to an aspect of the invention comprises an irradiation unit configured to generate at least one train of periodic pulses of electromagnetic energy, the pulses of the at least one train of periodic pulses exhibiting a predetermined pulse duration and repetition rate and the at least one train of periodic pulses exhibiting a predetermined train duration, and to irradiate a target with the at least one generated train of periodic pulses. The device further comprises a detection unit configured to detect acoustic waves generated in the target during and/or in response to irradiating the target with the at least one train of periodic pulses and to generate an according detection signal, the detection signal comprising, in particular for each train of the at least one train of periodic pulses, detection signal components at a plurality of discrete frequencies in the frequency domain, the discrete frequencies being spaced from each other by a frequency spacing corresponding to the predetermined repetition rate of the pulses of the at least one train of pulses. Further, a processing unit is configured to modify the detection signal in the frequency domain, preferably by modifying the detection signal components at the plurality of discrete frequencies and/or by modifying, in particular suppressing or attenuating, detection signal components at frequencies located between the plurality of discrete frequencies, to obtain a modified detection signal, which preferably contains modified detection signal components at the plurality of discrete frequencies, and to derive at least one property of the target based on the modified detection signal, preferably based on the modified detection signal components at the plurality of discrete frequencies.

The method according to another aspect of the invention comprises the following steps: irradiating a target with at least one train of periodic pulses of electromagnetic energy, the pulses of the at least one train of periodic pulses exhibiting a predetermined pulse duration and repetition rate and the at least one train of periodic pulses exhibiting a predetermined train duration, detecting acoustic waves generated in the target during and/or in response to irradiating the target with the at least one train of periodic pulses and generating an according detection signal, the detection signal comprising, in particular for each train of the at least one train of periodic pulses, detection signal components at a plurality of discrete frequencies in the frequency domain, the discrete frequencies being spaced from each other by a frequency spacing corresponding to the predetermined repetition rate of the pulses of the at least one train of periodic pulses, modifying the detection signal in the frequency domain, preferably by modifying the detection signal components at the plurality of discrete frequencies and/or by modifying, in particular suppressing or attenuating, detection signal components at frequencies located between the plurality of discrete frequencies, to obtain a modified detection signal, which preferably contains modified detection signal components at the plurality of discrete frequencies, and deriving at least one property of the target based on the modified detection signal, preferably based on the modified detection signal components at the plurality of discrete frequencies.

Preferably, the expression "a plurality of discrete frequencies" relates to at least 10, in particular at least 25 or at least 50 or at least 100, discrete frequencies. Preferably, the inverse of the product of the repetition rate of the pulses and the pulse duration is at least 10, 25, 50 or 100, whereby the detection signal comprises detection signal components at least 10, at least 25, at least 50 or at least 100 discrete frequencies in the frequency domain.

Preferably, the at least one property of the target, which is preferably derived from the modified detection signal components at the plurality of discrete frequencies, exhibits a spatial resolution in a direction, in particular a depth direction, which corresponds to the propagation direction (also referred to as "z" direction) of the electromagnetic energy towards and/or in the target. Thus, providing detection signal components at the plurality of discrete frequencies in the frequency domain advantageously allows for depth-resolved sensing, in particular imaging, of the target based on a single measurement, i.e. by irradiating the target with the train of periodic pulses and detecting the acoustic waves generated in response thereto, without the need to repeat the same measurement at different frequencies. Preferably, a pulse in the sense of present invention corresponds to a single or individual burst of electromagnetic energy exhibiting a predetermined amplitude or intensity for a finite, in particular short, time interval. A pulse is defined by its amplitude and duration.

Preferably, a train of pulses in the sense of present invention corresponds to a sequence of pulses, i.e. a successive occurrence of a finite number of pulses. A train of pulses is defined by the train duration, i.e. the duration of the sequence of pulses, and/or the finite number of pulses contained in the sequence.

Preferably, periodic pulses in the sense of present invention correspond to a repetitive occurrence of pulses at a regular time interval or period.

Preferably, a train of periodic pulses in the sense of present invention corresponds to a sequence of a finite number of pulses occurring repetitively at a regular time interval or period.

For example, the at least one property of the target relates to absorption of electromagnetic energy in the target, also referred to as optical absorption, and/or a concentration of one or more chromophores in the target. Preferably, the term "chromophore" relates to any kind of substances in the target which absorb electromagnetic energy generated by the irradiation unit.

For example, the at least one property of the target may be derived for a single location on or in the tissue, for a few or a plurality of locations on or in the tissue and/or may relate to a two- or three-dimensional map or image representative of optical absorption and/or presence and/or concentration of chromophore(s) in the tissue.

For example, the at least one property of the target relates to a two- or three-dimensional optoacoustic image of the target. Preferably, the optoacoustic image comprises a plurality of pixels exhibiting greyscale and/or color scale values.

A preferred aspect of the invention is based on the approach of irradiating a target with electromagnetic energy in a way that optoacoustic waves generated in the target in response to the irradiation comprise features characteristic of both frequency domain optoacoustic signals and time domain optoacoustic signals. That is, "hybrid" optoacoustic signals composed of well-defined multiple components are generated.

This is preferably achieved by modulating the electromagnetic energy to form a train of periodic pulses which causes an optoacoustic response, i.e. acoustic waves, in the target comprising components at a plurality of, in particular evenly distributed, frequencies of a discrete frequency spectrum in the frequency domain. While the discrete nature of the frequencies is characteristic of time domain optoacoustic sensing, the distribution of discrete frequencies over a spectrum is characteristic of frequency domain optoacoustic sensing. Hence, the present approach allows for the combination of advantages of both modalities.

In particular, irradiation of the target with a train of periodic pulses allows for higher duty cycles compared to pure time domain approaches. At the same time, components of the detection signal at the discrete frequencies allow for simple and reliable modifications of the detection signal or even single components in the frequency domain. Further, the multiple frequencies distributed over a spectrum render the need for frequency scanning, from which pure frequency domain approaches suffer, obsolete.

Features of the frequency spectrum, e.g. range and shape, of the generated optoacoustic signals can be chosen or adjusted by adjusting or selecting characteristics or parameters of the train of periodic pulses of the electromagnetic energy. Such characteristics or parameters may relate to the pulse duration, the repetition rate of pulses and/or the train duration. In particular, the spacing of discrete frequencies of the spectrum is governed by a predetermined periodicity, i.e. the repetition rate, of the pulses in the pulse train. By adjusting said characteristics or parameters, the sensitivity, speed and depth resolution of the device and method may be adapted to the needs of the particular application.

For example, it is possible to perform optoacoustic sensing, in particular imaging, in a first mode enabling high spatial resolution in a depth direction, which is preferably defined by the propagation direction of the electromagnetic energy towards and/or in the target, by decreasing the repetition rate of the pulses, whereby detection signal components at a higher number of frequencies are generated. Alternatively, it is possible to perform optoacoustic sensing, in particular imaging, in a second mode enabling high signal-to-noise ratio and high speed by increasing the repetition rate of the pulses, whereby the magnitude of the detection signal components at the plurality of frequencies is increased.

In summary, the invention allows for flexible and economic optoacoustic imaging, in particular optoacoustic imaging, with enhanced signal-to-noise ratio.

According to a preferred embodiment, the plurality of discrete frequencies are in a frequency range between a lowest frequency and a highest frequency, wherein the lowest frequency corresponds to the repetition rate of the pulses and/or the highest frequency is proportional to the reciprocal value of the pulse duration. Preferably, the highest frequency corresponds to a cut-off frequency above which detection signal components are below a threshold value, e.g. 3 dB. Preferably, the device further comprises a control unit configured to set or enabling a user to set the repetition rate of the pulses of electromagnetic energy generated by the irradiation unit and/or to set or enable a user to set the pulse duration of the pulses of electromagnetic energy generated by the irradiation unit. By that means, the frequency range of the detection signal in the frequency domain may be set to any desired range. Thereby, a sensing speed and/or a depth range, from which information contained in the detection signal may be obtained, can be easily and reliably adapted to the needs of the specific application and/or properties of the target, e.g. a particular speed of sound or attenuation of electromagnetic energy, such that high quality optoacoustic data, in particular images, can be generated.

In another preferred embodiment, the total number of detection signal components at the plurality of discrete frequencies contained in the detection signal corresponds to the inverse of the product of the repetition rate and the pulse duration. That is, the inverse of the product of the repetition rate and the pulse duration determines the number of discrete frequencies of detection signal components at which the detection signal may be sampled. For example, by decreasing the pulse duration the bandwidth of the spectrum of frequencies, i.e. the range of the frequency spectrum, over which the plurality of discrete frequencies is distributed, may be increased. Accordingly, a higher number of detection signal components at multiple, in particular equidistantly, spaced distinct frequencies is contained in the spectrum. Likewise, decreasing the repetition rate results in a decrease in the frequency spacing between the plurality of discrete frequencies of the detection signal components, i.e. a density of detection signal components per frequency range is increased. Accordingly, at a constant bandwidth of the spectrum, a higher number of detection signal components at multiple distinct frequencies is contained in the spectrum.

By setting the repetition rate and/or the pulse duration of the pulses of electromagnetic energy generated by the irradiation unit by means of the control unit, the resulting total number of the detection signal components at the plurality of discrete frequencies may be adjusted. Accordingly, as the total number of the detection signal components at the plurality of discrete frequencies defines the spatial resolution along a depth direction in the target, wherein the depth direction is preferably defined by the direction of propagation of the electromagnetic energy, the spatial resolution may be adjusted in a convenient and easy way.

In yet another preferred embodiment, the total number of pulses contained in the train of periodic pulses is between 5 and $10^4$, preferably between 10 and $7.5 \cdot 10^3$, in particular between 50 and $5 \cdot 10^3$. Preferably, the total number of pulses contained in the train of periodic pulses depends on the field of application of the device and method. For example, in order to generate optoacoustic images of the target, e.g. two- or three-dimensional maps of optical absorption and/or a concentration of chromophores, the total number of pulses contained in the train of periodic pulses is preferably between approx. 100 and approx. 1000. Alternatively, in order to determine a property of the target, e.g. optical absorption and/or concentration of chromophores at a single location or a few locations, preferably more than 1000, in particular more than 2000, pulses are contained in the train of periodic pulses.

Preferably, the processing unit is further configured to perform a processing of the detection signal generated when detecting the acoustic waves generated in the target during and/or in response to irradiating the target with the train of periodic pulses such that the at least one property of the target can be derived based on the processed and modified detection signal. In this way, a high signal-to-noise ratio of the modified detection signal may be achieved and hence the at least one property of the target can be determined with particularly high accuracy.

According to yet another preferred embodiment, the processing unit is configured to modify the detection signal in the frequency domain by filtering the detection signal in the frequency domain. The filtering may be performed by applying a filter function that is preferably adapted to the features of the frequency spectrum, in particular to the distribution of the detection signal components at the multiple frequencies. By that means, a particularly high signal-to-noise ratio of the detection signal can be achieved.

Alternatively or additionally, the processing unit is configured to modify the detection signal in the frequency domain by cross-correlating the detection signal with a predetermined signal (e.g. a detection signal to be expected) in the frequency domain, and to use the cross-correlated detection signal as the modified detection signal.

Alternatively or additionally, the processing unit is configured to modify the detection signal in the frequency domain by applying a matched filter to the detection signal in the frequency domain. This is preferably performed by correlating a predetermined detection signal, also referred to as template, with the detection signal to detect the presence of the template in the detection signal. This is equivalent to convolving the detection signal with a conjugated time-reversed version of the template. The matched filter is the preferred (optimal) linear filter for maximizing the signal-to-noise ratio (SNR) in the presence of additive stochastic noise.

In yet another preferred embodiment, the processing unit is configured to filter the detection signal in the frequency domain by filtering out and/or suppressing and/or attenuating signal components of the detection signal, in particular noise, at frequencies located between the plurality of discrete frequencies. Alternatively or additionally, signal components of the detection signal at the plurality of discrete frequencies may be let through. To achieve this filtering, the control unit may be configured to calculate the plurality of discrete frequencies of the detection signal components based on parameters of the train of periodic pulses, in particular based on the repetition rate and/or the pulse duration of the pulses. Preferably, the control unit is configured to transmit said calculated plurality of discrete frequencies of the detection signal components to the processing unit, based on which the filtering may be performed.

By that means, the signal-to-noise ratio of the detection signal can be increased in a particularly effective way.

Alternatively or additionally, the filtering may be performed by applying a filter function configured to accept or pass peaks in the detection signal and to reject all other components of the detection signal. By that means, the sensitivity of the filter function can be easily set, allowing for a flexible adaption of the filtering to the needs of the user or to properties of the target.

In yet another preferred embodiment, the detection unit is configured to detect the acoustic waves in the time domain and to generate the according detection signal in the time domain, and the processing unit is configured to transform the detection signal into a transformed detection signal in the frequency domain and to modify the transformed detection signal in the frequency domain to obtain the modified detection signal. By acquisition of data in the time domain, a single sampling device configured to record multiple frequencies and/or wavelengths may be used.

Preferably, the processing unit is configured to transform the detection signal into the transformed detection signal in the frequency domain by means of a Fourier transformation. Alternatively, another time-frequency transformation, for example including wavelets or other bases, may be utilized.

By means of the transformation of the detection signal into the frequency domain, modifications of the detection signal, in particular to components of the detection signal at the plurality of discrete frequencies, can be performed easily and reliably.

According to yet another preferred embodiment, the detection unit is configured to detect the acoustic waves in the frequency domain. By that means, additional transformation processes to transform the detection signal into the frequency domain, which may bias the detection signal, are not necessary. In particular, a detection of the acoustic waves in the frequency domain allows a speed-up of the optoacoustic sensing, in particular imaging.

According to yet another preferred embodiment, the detection unit comprises at least one of the following: a spectrum analyzer configured to measure the magnitude of the detection signal versus frequency, a lock-in amplifier configured to detect signal components of the detection signal at the plurality of discrete frequencies, and an I/Q demodulator configured to detect amplitude and phase of the signal components of the detection signal at the plurality of discrete frequencies. By these means, it is possible to provide the detection signals at the processing unit in a fast and reliable way. Further, any one of the spectrum analyzer, the lock-in amplifier and the I/Q demodulator is suited to generate the detection signal with an already high signal-to-noise ratio.

In another preferred embodiment, at least one of the following applies: the pulse duration of the pulses is between 0.5 ns and 100 ns, in particular between 1 ns and 10 ns, the repetition rate of the pulses is between 1 MHz and 200 MHz, in particular between 10 MHz and 100 MHz, and the train duration of the train of periodic pulses is between 3 μs and 300 ms, in particular between 50 μs and 10 ms. The mentioned values of the pulse duration result, on the one hand, in a sufficiently large bandwidth, i.e. the range of the frequency spectrum of the detection signal components, and corresponding high spatial resolution in a depth direction in the target and, on the other hand, in a magnitude of the detection signal components at the plurality of discrete frequencies which is large enough to reliably distinguish between noise and the detection signal components, in particular when filtering the detection signal in the frequency domain. Likewise, the mentioned values of the repetition rate result in a sufficiently large number of detection signal components at the plurality of discrete frequencies in the frequency spectrum and corresponding high spatial resolution in the depth direction in the target, while at the same time the magnitude of the detection signal components at the plurality of discrete frequencies is large enough to reliably distinguish between noise and the detection signal components. Moreover, the mentioned values of the train duration allow for sufficient data generated by the detection unit that can be averaged in order to derive the at least one property of the target in a particularly reliable way.

Preferably, the pulse duration of the pulses, the repetition rate of the pulses and/or the train duration of the train of periodic pulses, in particular in conjunction with an output energy of the irradiation unit, e.g. 100 mW, is chosen such that an amount of total energy deposited in the target complies with the ANSI safety limits. In particular, the above-mentioned parameters are preferably chosen such that the total energy deposited in the target is less than 500 mJ, preferably less than 100 mJ, in particular less than 10 mJ.

In yet another preferred embodiment, the detection unit exhibits a sensitivity field corresponding to an area or volume in which the detection unit is sensitive to acoustic waves, and the irradiation unit is configured to focus the electromagnetic energy on a focus area or focus volume on or in the target, wherein the sensitivity field of the detection unit is smaller than and/or located within the focus area or focus volume. Preferably, the detection unit or parts thereof are arranged and/or configured such that the sensitivity field of the detection unit coincides with an area of interest in the target. By this means, the magnitude of the detection signal components at the plurality of discrete frequencies of the detection signal is increased, such that a particularly high signal to noise ratio can be achieved.

According to yet another preferred embodiment, the irradiation unit comprises a laser diode designed for a continuous emission of electromagnetic energy at a predetermined power level, and a laser diode driver configured for driving the laser diode to emit a train of periodic pulses of electromagnetic energy for irradiating the target at a power level which is above the predetermined power level. By this means, short pulses of electromagnetic energy with high energy density and at wavelengths in the visible or infrared spectrum, in particular in between 300 nm and 1500 nm, preferably between 300 nm and 900 nm, can be generated. Using electromagnetic energy in this spectrum is particularly advantageous for optoacoustic sensing or imaging of certain targets, in particular mammalian tissue, due to the absorption properties of these targets.

Preferably, the predetermined power level corresponds to an absolute maximum power in continuous emission, which in one embodiment lies above 0.5 W, preferably above 1 W, in particular above 3 W. By driving the laser diode accordingly, the pulses of the train of periodic pulses may provide more than 100 nJ, preferably more than 150 nJ, in particular more than 200 nJ of energy per pulse, wherein each pulse may provide an optical peak power of more than 5 W, preferably above 10 W, in particular above 20 W.

According to yet another embodiment, the laser diode driver comprises a capacitor electrically connected to the laser diode via a resistor, a voltage supply configured to charge the capacitor, and a power switch configured to close a current loop comprising the capacitor and the laser diode. The power switch, for example a MOSFET, is preferably triggered by means of an external transistor-transistor logic pulse, wherein a trigger frequency preferably corresponds to 25 kHz and above, more preferably to 100 kHz and above, most preferably to 1 MHz and above, in particular 100 MHz and above.

It is moreover preferred, that the capacitor and the power switch are configured to operate at a Voltage of 100 V and above, preferably at 250 V and above, in particular at 500 V and above. Accordingly, the voltage supply is configured to charge the capacitor at a Voltage of 100 V and above, preferably at 250 V and above, in particular at 500 V and above.

By means of one or more of the above-mentioned embodiments, a train of periodic high-power pulses of electromagnetic energy can be generated by the laser diode, resulting in an enhanced signal-to-noise ratio of the detection signals.

According to yet another preferred embodiment, the at least one property of the target may be derived from modified detection signals, which are obtained from more than one train of periodic pulses. In this embodiment, the target is preferably irradiated with two or more trains of periodic pulses of electromagnetic energy, wherein the pulses of the two or more trains exhibit at least one predetermined repetition rate. Acoustic waves generated in the target during or in response to irradiating the target with the two or more trains of periodic pulses are detected and converted into according detection signals comprising detection signal components at a plurality of discrete frequencies in the frequency domain, wherein the discrete frequencies are spaced from each other by a frequency spacing corresponding to the at least one predetermined repetition rate of the pulses of the two or more pulse trains. After modifying the detection signals in the frequency domain, the at least one property of the target can be derived from the modified detection signals.

According to a preferred embodiment, the irradiation unit is configured to generate at least two trains of periodic pulses of electromagnetic energy at different electromagnetic wavelengths or wavelength ranges, the pulses of the at least two trains of periodic pulses exhibiting different repetition rates, and to, in particular simultaneously, irradiate the target with the at least two trains of periodic pulses. Preferably, the detection unit is configured to detect acoustic waves generated in the target in response to irradiating the target with the at least two trains of periodic pulses and to generate an according detection signal comprising at least two series of detection signal components at a plurality of discrete frequencies in the frequency domain, wherein the discrete frequencies of each series of detection signal components are spaced from each other by a frequency spacing which corresponds to the repetition rate of the pulses of the respective train of periodic pulses and is, therefore, different for each series. Preferably, the processing unit is configured to modify the detection signal in the frequency domain, in particular to modify at least one of the series of the detection signal components at the plurality of discrete frequencies, to obtain a modified detection signal, and to derive the at least one property of the target based on the modified detection signal.

In this embodiment, additionally or alternatively to irradiating the target with only one train of pulses of electromagnetic energy at a single electromagnetic wave-length or wavelength range, it is preferred to simultaneously irradiate the target with at least two trains of pulses of electromagnetic energy at different electromagnetic, in particular optical, wavelengths or wavelengths ranges, wherein the pulses of the at least two pulse trains exhibit, preferably slightly, different repetition rates. As a result, at least two series of detection signal components at a plurality of discrete frequencies in the frequency domain are obtained simultaneously. Because of the different repetition rates, the discrete frequencies of each series of the detection signal components are spaced from each other by frequency spacings, which are different for the at least two series. For example, the distance between two neighboring detection signal components of a first series of detection signal components corresponds to a first repetition rate of the pulses of a first train of pulses of electromagnetic energy at a first wavelength, and the distance between two neighboring detection signal components of a second series of detection signal components corresponds to a second repetition rate of the pulses of a second train of pulses of electromagnetic energy at a second wavelength. Thus, the different responses of the target to electromagnetic energy at different wavelengths (e.g. at the first and second wavelength in the aforementioned example) is contained in the very same and/or single frequency spectrum and can be, after optional modifying and/or filtering, easily and reliably identified and/or evaluated, e.g. based on the magnitude(s) of the differently spaced detection signal components. This approach is also referred to as multispectral pulse train frequency domain (MS-PTFD) optoacoustics.

Preferably, the irradiation unit comprises at least two radiation sources, e.g. lasers, each of which being configured to emit a train of pulses at a desired electromagnetic wavelength or wavelength range at a desired repetition rate, wherein the wavelengths or wavelength ranges and repetition rates of the at least two trains of pulses are different. For example, a first radiation source generates a first train of pulses of electromagnetic energy at a first electromagnetic wavelength and has a first repetition rate, and a second radiation source generates a second train of pulses of electromagnetic energy at a second electromagnetic wavelength and has a second repetition rate, wherein both the first and second wavelengths and the first and second repetition rates are different.

Usually, multispectral optoacoustic methods are based on time sharing. This means that a laser pulse of a particular optical wavelength is used to interrogate the target, followed by a laser pulse of the next desired wavelength etc. This process is repeated for all wavelengths, causing an increase of the measurement time proportional to the number of wavelength used. When an optical parametric oscillator used, the total repetition rate is limited, typically to below a few 100 Hz. This puts an even more severe limit on the achievable scan times and the number of wavelength that can be interrogated. The preferred MS-PTFD optoacoustic approach provides a solution to this trade-off by replacing time sharing with frequency sharing, wherein preferably at least two lasers at different optical wavelengths are deployed simultaneously, but at slightly different repetition rates of the respective pulse trains. The detection of the optoacoustic effect caused by these laser pulse trains takes place with the same detection unit (transducer). This will result in the frequency components of each laser pulse train to occupy different frequency bins. As the resulting frequency components of each laser pulse train are multiples of the respective repetition rate, they can be assigned to the appropriate laser pulse train and the respective optical wavelength.

For example, the target is irradiated with two different pulse trains, both featuring 20 ns long pulses at two different repetition rates of 1 MHz and 1.01 MHz.

For example, different electromagnetic wavelengths or wavelength ranges of the pulse trains may be at or, respectively, around 445 nm, 465 nm, 638 nm and/or 808 nm.

Preferably, the different repetition rates are chosen such that the frequency components obtained for the two laser pulse trains do not occupy the same bin in the frequency domain. Preferably, for this purpose the limited detection bandwidth of the detection unit (transducer) is considered. Preferably, the repetition rate is chosen such that the frequency components do not overlap within the transducer bandwidth.

Alternatively or additionally, the difference of the repetition rates is preferably chosen to avoid detection signal components of the two or more series (resulting from the two or more pulse trains) from overlapping in the interrogated bandwidth. For example, the lower the difference of the repetition rates, the closer the detection signal components of the at least two series will lie together in the lower end of the frequency spectrum. Hence, a minimum frequency difference is to be observed by the detection unit. On the other hand, the higher the difference of the repetition rates, the faster the frequency difference of the detection signal components of the at least two series will grow. As a result, there may be an overlay between two adjacent components of different series. For example, if the repetition rates are 1 MHz (first pulse train) and 1.1 MHz (second pulse train), the $11^{th}$ detection signal component resulting from the first pulse train will overlay with the $10^{th}$ detection signal component of the second pulse train at 11 MHz. That is, if the interrogated bandwidth and/or detection bandwidth of the detection unit (transducer) is within a range of, e.g., approx. 1 MHz to 10 MHz, the detection signal components of the two series do not overlap within this bandwidth and are, therefore, distinguishable.

For sake of simplification, only two lasers for simultaneously irradiating the target with pulse trains of different electromagnetic energies (wavelengths) and repetition rates were mentioned above. However, it is preferred to provide more than two radiation sources, e.g. three, four, five or even more lasers, for simultaneously irradiating the target with three, four, five or even more different pulse trains of different electromagnetic energies (wavelengths) and repetition rates. For example, it is possible to provide four radiation sources emitting pulsed electromagnetic radiation at or, respectively, around 445 nm, 465 nm, 638 nm and/or 808 nm at a pulse repetition rate of 200 kHz, 200.125 kHz, 200.250 kHz and 200.375 kHz, respectively. The above and other elements, features, characteristics and advantages of the present invention will become more apparent from the following detailed description of preferred embodiments with reference to the attached figures showing:

Figure 1:
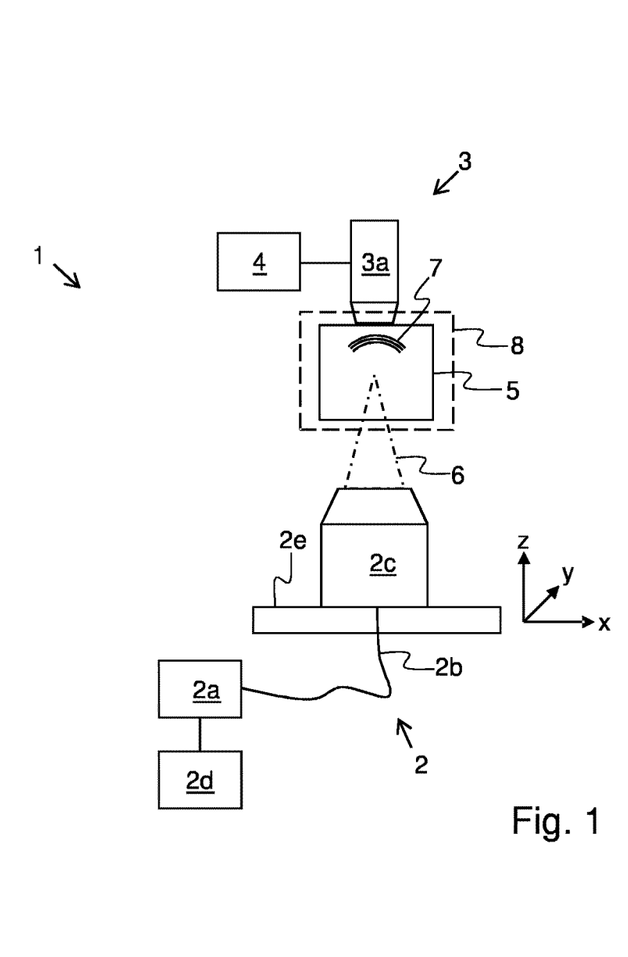
FIG. 1 an example of a device for optoacoustic sensing or imaging.

FIG. 1 shows an example of a device 1 for optoacoustic sensing or imaging of a target 5 operating in trans-illumination mode and comprising an irradiation unit 2a to 2e, a detection unit 3a and a processing unit 4.

The irradiation unit comprises an irradiation source 2a, e.g. a laser diode operating at a wavelength of 450 nm, coupled via a fiber 2b to an objective 2c, e.g. a microscopy objective. The laser diode is driven by a, preferably analogue, laser driver 2d to emit periodic pulses of electromagnetic energy 6, e.g. Gaussian pulses with full width at half-maximum of 25 ns at a repetition rate of 2 MHz. The objective 2c is mounted on a translation stage 2e to adjust the focal point of the objective 2c in the target 5, preferably along the z-axis.

The electromagnetic energy 6 focused on or in the target 5 generates acoustic waves 7 in the target 5 which are detected by an ultrasonic transducer 3a of the detection unit. Preferably, the transducer 3a, e.g. a spherically focused transducer operating at 25 MHz, is at least partially immersed in a coupling medium 8, e.g. water, which at least partially surrounds the target 5. The transducer 3a exhibits a sensitivity field corresponding to an area or volume, including the focus of the transducer 3a, in which the transducer 3a is sensitive to acoustic waves. In a preferred embodiment, the focal point of the objective 2c is located within the sensitivity field of the transducer 3a.

The transducer 3a generates a detection signal corresponding to the detected acoustic waves 7. The detection signal is provided to the processing unit 4 for analysis and/or processing.

Alternatively, the device 1 for optoacoustic sensing or imaging may be configured to operate in a so-called epi-illumination mode, in which the objective 2c and the transducer 3a are arranged next to each other, facing the target 5 from the same side (not shown). In this arrangement, the objective 2c is preferably tilted with respect to the transducer 3a. The objective 2c and transducer 3a may be mounted on the translation stage 2e which is preferably configured to translate the objective 2c and the transducer 3a in an x-y-plane perpendicular to the z-axis, whereby the target 5 is sensed by raster scanning.

The laser diode 2a is preferably operated by a trigger signal generated by a function generator and irradiates the target 5 with light at a wavelength of approx. 450 nm. Light emitted by the laser diode 2a is preferably coupled into a multimode glass fiber 2b with a diameter of approx. 400 μm and numerical aperture (NA) of approx. 0.5. The light exiting the fiber 2b may be fed through a collimator into focusing optics 2c mounted on a kinematic mount.

The pulse energy emitted towards the target 5 may be approx. 72 nJ. Preferably, the transducer 3a is spherically focused with 29 MHz central frequency, 112% relative bandwidth, 3 mm focal length and 0.5 NA. In one embodiment, the signal from the transducer 3a is fed into a 60 dB gain amplifier and digitized with 12-bit resolution at 200 Ms/s. The digitized data may be stored on a solid-state drive for further processing and/or analysis. Preferably, the entire system is controlled using a custom-designed application, e.g. coded in MATLAB.

Figure 2:
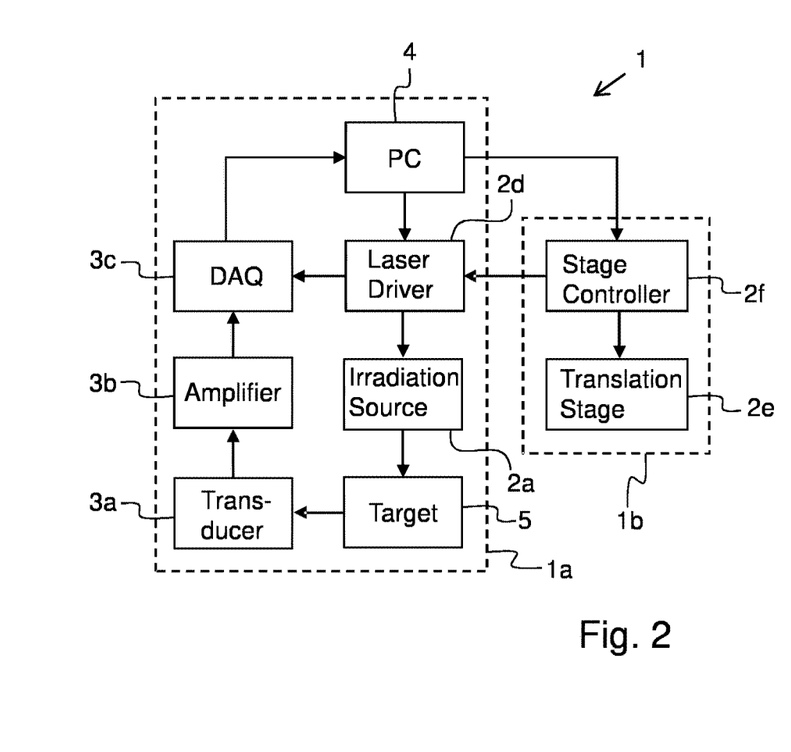
FIG. 2 a first example of a schematic setup of a device for optoacoustic sensing or imaging.

FIG. 2 shows a first example of a schematic setup of a device 1 for optoacoustic sensing or imaging. The device 1 comprises a signal generation and acquisition unit 1a and a scanning unit 1b. The signal generation and acquisition unit 1a comprises a processing unit 4, e.g. a computer (PC), operatively coupled to laser driver 2d and stage controller 2f for controlling irradiation source 2a, e.g. a laser diode, and translation stage 2e, respectively.

Preferably, the irradiation source 2a is coupled to target 5 by means of an irradiation optics, which is preferably mounted onto the translation stage 2e, and configured to transmit electromagnetic energy onto or into the target 5, whereby acoustic waves are generated in the target 5.

The acoustic waves are detected by transducer 3a, which generates according detection signals. The detection signals are amplified by means of amplifier 3b, e.g. a 60 dB amplifier, and acquired by data acquisition (DAQ) card 3c.

Figure 3:
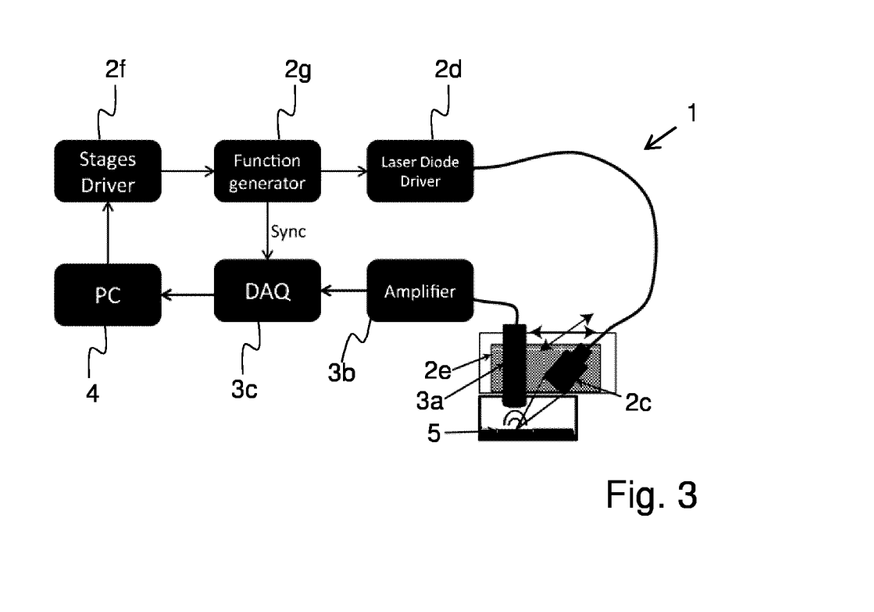
FIG. 3 a second example of a schematic setup of a device for optoacoustic sensing or imaging.

FIG. 3 shows a second example of a schematic setup of a device 1 for optoacoustic sensing or imaging in epi-illumination mode. The objective 2c and the transducer 3a are mounted on translation stage 2e and arranged next to each other to face the target 5 from above. Preferably, the objective 2c is tilted with respect to the transducer 3a. The translation stage 2e is preferably configured to translate the objective 2c and the transducer 3a in an x-y-plane whereby the target 5 is sensed by raster scanning.

The device 1 comprises a processing unit 4 which is configured to control stage driver 2f for controlling the position of the translation stage 2e. During raster scanning, the translation stage 2e is moved to a desired starting position where-upon line-by-line scanning in a line-scanning direction is performed at a constant speed, which is preferably equal to the desired step size of the line scan divided by the integration time of the ultrasound transducer 3a. Integration time is the number N of pulses to be acquired divided by the pulse repetition rate.

Every time the translation stage 2e translates one step size, the stage driver 2f initiates the acquisition of one A-scan by sending a trigger signal to function generator 2g, which then sends a chain of N pulses to a laser driver 2d at the desired repetition rate. Simultaneously, the function generator 2g initiates data acquisition by sending a trigger signal to a data acquisition (DAQ) card 3c which then acquires data, preferably at 200 Ms/s. The data comprises detection signals generated by the transducer 3a in response to the detected ultrasonic waves, which are amplified by means of an amplifier 3b.

This process is repeated every time a line-scanning mechanism of the translation stage 2e moves the translation stage 2e by one step size. When the translation stage 2e reaches its final position at the end of a line to be scanned, a column-scanning mechanism of the translation stage 2e moves the translation stage 2e together with the objective 2c and the transducer 3a one step size in a direction perpendicular to the line-scanning direction. Then, the next line is scanned as described above and so on. Preferably, the obtained data is streamed to a solid-state drive processing unit 4 and stored for further processing.

Figure 4:
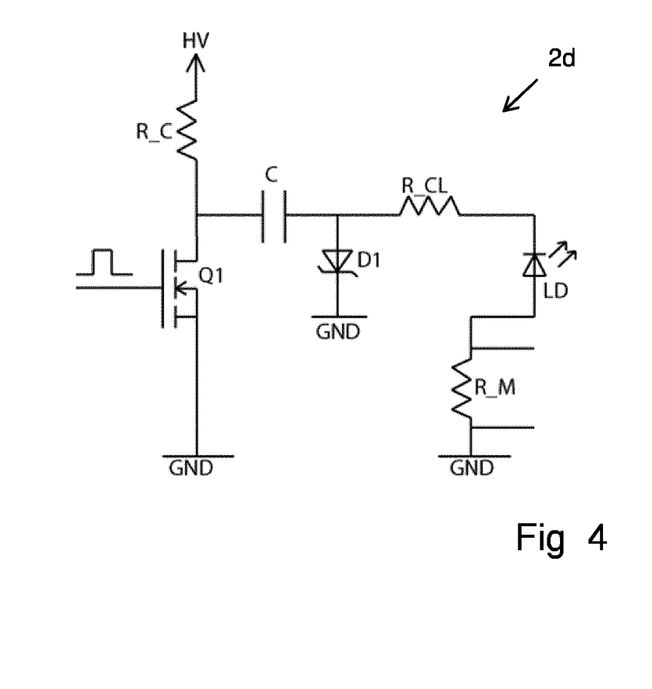
FIG. 4 an example of a laser diode driver.

FIG. 4 shows an example of a laser driver 2d which is configured to deliver high-current nanosecond pulses for driving the irradiation source 2a (see FIGS. 1 and 2), in particular a laser diode LD.

The working principle is as follows: Capacitor C is charged at high voltage HV by applying the voltage between resistor $R_c$ and diode $D_1$. A trigger signal of a function generator (not shown), e.g. an external Transistor-Transistor-Logic (TTL) pulse, triggers power MOSFET $Q_1$. If the power MOSFET $Q_1$ conducts, the capacitor C is discharged via laser diode LD. Preferably, the capacitor C and the power MOSFET $Q_1$ can operate at voltages up to 500 V. Resistor $R_{CL}$ limits the current to the desired value. This design allows the current amplitude to be controlled through the high voltage amplitude. The rise time of the current pulse is determined by the turn-on speed of the power MOSFET $Q_1$, while the fall time is determined only by the time constant of the circuit given by $R_{CL}$, C, LD and $Q_1$. By means of this design, the pulse duration of a pulse of electromagnetic energy emitted by the laser diode LD can be controlled by changing the capacitance value of the capacitor C.

By means of the laser driver 2d it is possible to operate continuous wave (CW) laser diodes in pulsed mode, preferably generating pulses of electromagnetic energy in the visible spectrum of 10 ns duration, with 200 nJ energy per pulse and repetition rates above 600 kHz without damaging the CW laser diode. Compared to pulse-operated laser diodes, continuous wave (CW) laser diodes have a broader wavelength availability and are less expensive, which makes them attractive for optoacoustic sensing.

Figure 5:
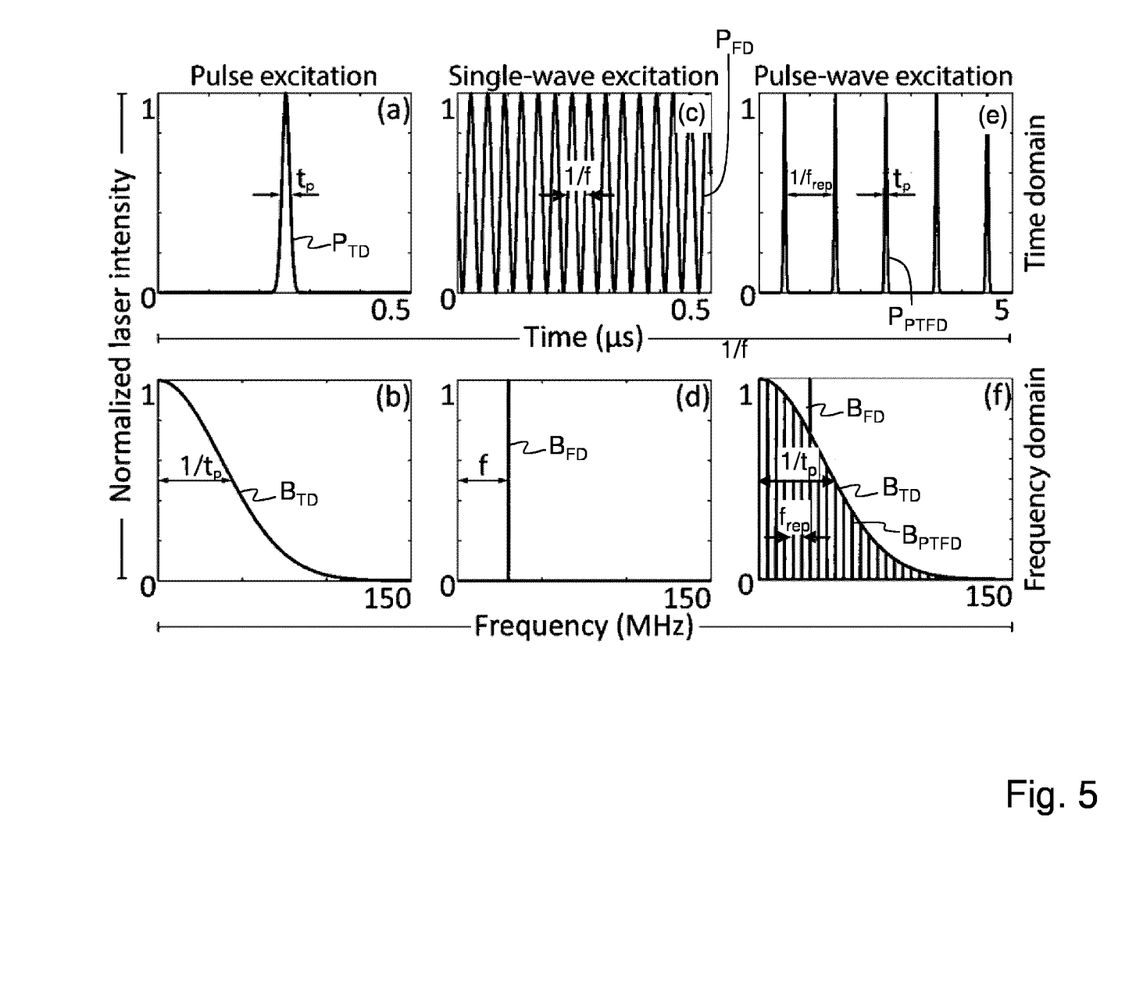
FIG. 5 examples of excitations in time domain and according frequency components in frequency domain.

FIG. 5 shows examples of excitations in time domain (TD) and their frequency components in frequency domain (FD).

As illustrated in FIGS. 5(a) and 5(b), a single pulse $P_{TD}$ of a given duration $t_p$ in TD will cause a continuous frequency response with a bandwidth $B_{TD}$ corresponding to $1/t_p$ in FD. While this frequency response contains depth information with a high spatial resolution, single pulses $P_{TD}$, in particular short pulses corresponding to wideband frequency responses, do not allow for efficient background noise filtering.

In FD optoacoustics, light sources are amplitude-modulated in TD, e.g. by a sinusoidal waveform $P_{FD}$ exhibiting a frequency f and periodic time 1/f of the modulation as shown in FIG. 5(c). This modulation causes an optoacoustic response including a single frequency component $B_{FD}$ at the frequency f in FD that can easily be filtered from the background noise as illustrated in FIG. 5(d). However, scanning multiple modulation frequencies slows down data acquisition.

Rather than providing single-pulse excitation or single-wave excitation, according to a preferred aspect of present invention a train of nanosecond pulses of electromagnetic energy is provided, which is also referred to as pulse train frequency domain (PTFD) optoacoustics.

As illustrated in FIG. 5(e), in PTFD optoacoustics the target is irradiated in TD by a train of individual pulses $P_{PTFD}$ of electromagnetic energy, wherein the temporal spacing of the pulses $P_{PTFD}$ is determined by the repetition rate of the pulse train $r=1/f_{rep}$, and each of the pulses $P_{PTFD}$ exhibits a, preferably short, pulse duration $t_p$. Preferably, the pulse train is a strictly periodic function. As shown in FIG. 5(f), during or in response to irradiating the target with the pulse train acoustic waves are generated in the target which, in the FD, exhibit a sequence of discrete frequency components $B_{PTFD}$, which are spaced apart at a frequency $f_{rep}=1/r$ determined by the repetition rate r of the pulse train. The amplitude of the components $B_{PTFD}$ corresponds to the envelope $B_{TD}$ of a single pulse $P_{TD}$.

Hence, present PTFD approach combines the high information value of TD optoacoustics with the noise filtering potential of FD optoacoustics. As a result, the signal to noise ratio (SNR) and depth resolution are comparable or even better than those obtained by pure TD approaches. Because the excitation pattern in PTFD optoacoustics is, preferably strictly, periodic, its Fourier transform exhibits a plurality of discrete spikes at frequencies corresponding to the pulse repetition rate and its multiples. This allows for a clear separation between signal and background noise components in between the spikes, wherein subsequent filtering of the noise yields higher SNR compared to TD optoacoustic sensing or imaging approaches. This is further illustrated hereinafter.

Figure 6:
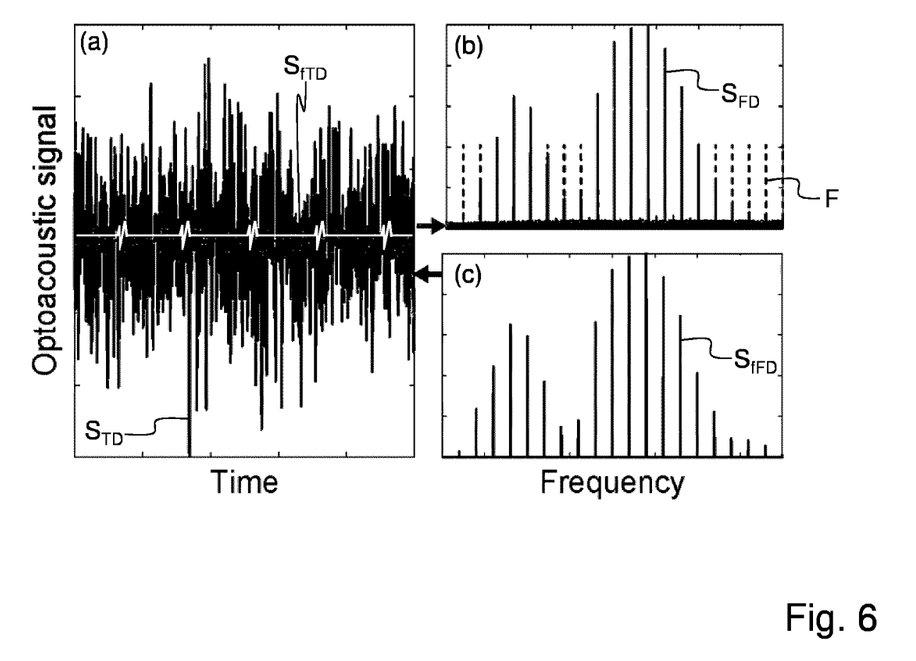
FIG. 6 an example of optoacoustic signal intensities in time domain (a) and frequency domain (b) and (c)

FIG. 6 shows examples of signal intensities in time and frequency domain to illustrate the concept of signal acquisition and noise reduction according to the PTFD optoacoustic approach.

FIG. 6(a) shows a raw PTFD detection signal $S_{TD}$ (black line) in TD generated by detecting acoustic waves produced in a target in response to transmitting electromagnetic energy into the target. The detection signal $S_{TD}$ is transferred into FD as shown in FIG. 6(b), resulting in a transformed detection signal $S_{FD}$ with multiple discrete frequency components determined by the repetition rate $f_{rep}$ of the pulse train $P_{PTFD}$ (cf. FIGS. 5(e) and (f)).

Because the transformed detection signal $S_{FD}$ in the FD contains main components only at multiple discrete frequencies, a filter function F (indicated by dashed lines) accepting signal components at the discrete frequency components and/or rejecting noise, in particular in between the discrete frequency components, can be easily applied to the transformed detection signal $S_{FD}$.

As shown in FIG. 6(c), by applying the filter function F to the transformed detection signal $S_{FD}$ a modified, i.e. filtered, transformed detection signal $S_{fFD}$ is obtained which contains significantly reduced noise. The modified transformed detection signal $S_{fFD}$ may be transferred back into TD to form a modified detection signal $S_{fTD}$ (see white line in FIG. 6(a)) which allows for precisely deriving at least one property of the target. Alternatively or additionally, at least one property of the target may be derived based on the modified transformed detection signal $S_{fFd}$ in FD.

The lowest frequency contained in FD caused by the pulse train $P_{PTFD}$ corresponds to the repetition rate $f_{rep}$ of the pulses in the pulse train $P_{PTFD}$ (cf. FIGS. 5(e) and (f)). Further, the repetition rate $f_{rep}$ defines the field of view, analogously to TD sensing.

The highest frequency contained in FD corresponds or is proportional to the reciprocal pulse duration $1/t_p$. The number of sampling points corresponds to the ratio between the repetition rate and the highest frequency, i.e. the reciprocal pulse duration. This corresponds to the axial resolution.

Increasing the repetition rate at a given pulse duration results in a decrease of the bandwidth $B_{TD}$. At the same time, the energy is concentrated in a lower number of frequency components $B_{PTFD}$, resulting in a higher SNR, because the same energy is distributed over a lower number of spikes.

Decreasing the pulse duration will yield a higher bandwidth $B_{TD}$. This results in more available frequency components $B_{PTFD}$, as the spacing between two components $B_{PTFD}$ corresponds to the repetition rate, which remains unchanged. As more frequency components $B_{PTFD}$ are available, a higher spatial resolution results.

Figure 7:
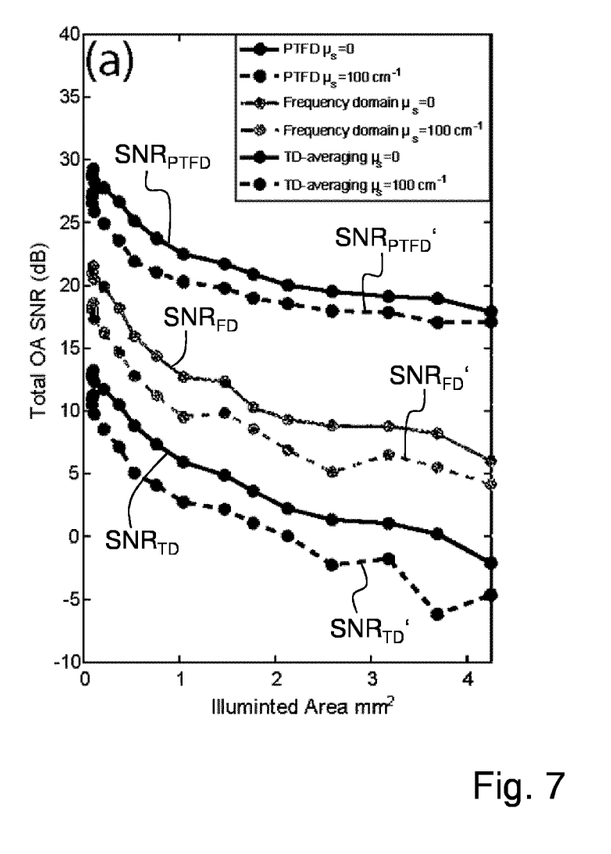
FIG. 7 examples of signal to noise ratios obtained with different optoacoustic methods.

FIG. 7 shows examples of signal to noise ratios (SNR) in order to illustrate the relative performance of time domain (TD), frequency domain (FD) and pulse train frequency domain (PTFD) optoacoustic sensing.

In present example, a device for optoacoustic sensing or imaging like the device 1 shown in FIG. 1 generates detection signals corresponding to the acoustic waves generated in a target, e.g. a 100 μm surgical suture, during irradiation with light, e.g. with an optical power of 100 mW. Preferably, the target is exposed for 100 ms, corresponding to a total deposited energy of 10 mJ.

To characterize the performance of PTFD, the laser is controlled to emit a train of pulses, e.g. of 25 ns duration and 50 nJ energy at a repetition rate of 2 MHz. The resulting detection signal is processed according to the method described with reference to FIG. 6(a) to (c), which yields a modified detection signal with high signal to noise ratio SNR$_{PTFD}$. For comparison, the detection signal is coherently averaged in TD, whereby an averaged signal is generated exhibiting a signal to noise ratio SNR$_{TD}$. Further, upon irradiating the target with light, which is amplitude-modulated by a sinusoidal signal at 24 MHz (cf. FIG. 5(*c*), P$_{FD}$), and subjecting the obtained detection signal to a Fourier transformation, a single frequency component at 24 MHz (cf. 5(*d*), B$_{FD}$) is obtained. The component is isolated, i.e. filtered, and converted back into TD to yield an accordingly modified signal exhibiting a signal to noise ratio SNR$_{FD}$.

In FIG. 7 the resulting signal to noise ratios SNR$_{PTFD}$, SNR$_{TD}$, SNR$_{TD}$ are plotted versus the size of the illuminated area of the target. Obviously, the PTFD optoacoustic approach results in considerably higher signal to noise ratios compared to the FD and TD approaches. Further, reducing the illuminated area increases the obtainable SNR for all three approaches. Apparently, for very small illuminated areas, the increase in SNR is disproportionate with respect to the decrease in illuminated area. It is, therefore, preferred to decrease the illuminated area in order to further enhance the signal to noise ratio obtained by the PTFD approach.

As also apparent from FIG. 7, the above applies accordingly to signal to noise ratios SNR$_{PTFD}$', SNR$_{TD}$' and SNR$_{FD}$' obtained at an increased scattering in a coupling medium, wherein the scattering coefficient $\mu_s$=100 cm$^{-1}$.

Preferably, in raster scanning applications of PTFD optoacoustic sensing or imaging typically non-averaged A-scans at 200×200 positions are measured at a step size of 25 μm to resolve image structures spatially extending to about 20 μm or 30 μm. The electromagnetic energy irradiated towards the target preferably consists of 5000 pulses with 12 ns pulse length at a repetition rate of 625 kHz. Data generated from detection signals are averaged and processed using a TD back-projection algorithm. Image quality is superior for TD averaging when a relatively small number of pulses, e.g. 5 pulses, are averaged, similar for TD and PTFD at intermediate numbers of averaged pulses e.g. 10 to 100 pulses, and it is superior in PTFD at relatively high numbers of pulses, e.g. 1000 or more pulses.

Depending on the desired number of averaged pulses, an acquisition time for such data is between 20 and 100 s, corresponding to an average of about 300 to 500 A-scans per second. However, for slower repetition rates, e.g. of 250 kHz, and an increased field of view, the acquisition time may rise up to 10 minutes.

PTFD imaging using a millisecond-long train of nanosecond pulses generated by a laser diode provides better SNR than FD imaging using single-frequency excitation. Also, for a given pulse energy, PTFD imaging provides superior SNR to conventional TD imaging when averaging a large number of pulses. Another particular advantage of the PTFD approach over conventional FD optoacoustics is that a pulse train maximizes the rate of change in light flux and hence the efficiency with which the optoacoustic signal, i.e. the acoustic wave, is generated. At the same time, optoacoustic signals at several frequencies are being generated. Multiple frequencies allow for depth-resolved imaging without having to repeat the same measurement at different frequencies, which is necessary with conventional FD approaches.

Modulating the laser amplitude, of a mean laser power of 100 mW, with a sinusoid waveform at 25 MHz, as it is done in FD, results in a rate of change in electromagnetic radiation flux of I$_{max}$·ω=30.41 mW/ns, and the resulting optoacoustic signal corresponds to 2212 counts. In contrast, when the laser is modulated with Gaussian pulses lasting 25 ns at a repetition rate of 2 MHz, the rate of change in flux is I$_{max}$/t$_{rise}$=62.5 mW/ns, and the resulting optoacoustic signal corresponds to 14570 counts. Hence, increasing the rate of change in electromagnetic radiation flux by a factor of 2 in PTFD optoacoustic sensing or imaging boosts the optoacoustic signal by a factor of 6.5.

Figure 8:
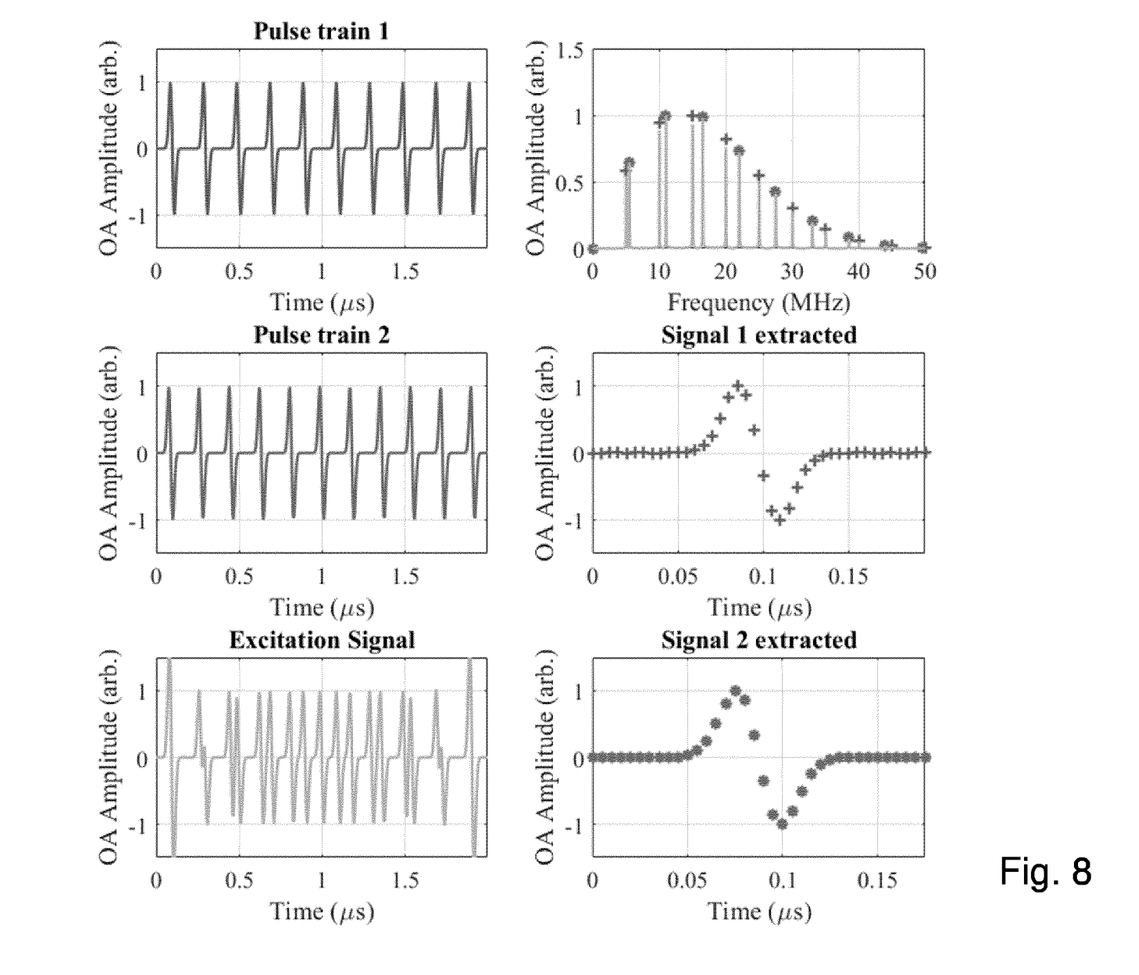
FIG. 8 examples of optoacoustic signal intensities in time and frequency domain for illustrating MS-PTFD optoacoustic sensing.

FIG. 8 shows examples of optoacoustic signal amplitudes in time and frequency domain for illustrating the principle of multispectral pulse train frequency domain (MS-PTFD) optoacoustic sensing.

Alternatively to irradiating the target 5 with only one train of pulses of electromagnetic energy at a single electromagnetic wavelength or wavelength range, with MS-PTFD optoacoustic sensing the target 5 is simultaneously irradiated with at least two trains of pulses (see "Pulse train 1" and "Pulse train 2" in FIG. 8) of electromagnetic energy at different electromagnetic wavelengths or wavelengths ranges, wherein the pulses of the at least two pulse trains exhibit, preferably slightly, different repetition rates.

Preferably, the "Pulse train 1" is provided by a first laser emitting at a first wavelength, and the "Pulse train 2" is provided by a second laser emitting at a second wavelength, which is different to the first wavelength.

Due to the simultaneous irradiation of the target 5 with the at least two pulse trains, the resulting irradiation signal (see "Excitation signal") corresponds to a sum or superposition of the at least two pulse trains, in present example a sum or superposition of "Pulse train 1" and "Pulse train 2".

In response to irradiating the target 5 in this way, the target 5 generates and emits acoustic waves 7 which are detected by the detection unit 3*a* and subsequently subjected to a Fourier transformation, whereby at least two series of detection signal components at a plurality of discrete frequencies in the frequency domain (see top right diagram of FIG. 8) are obtained simultaneously.

In present example, the frequency spectrum of the optoacoustic response of the target 5 contains both a first series of detection signal components obtained in response to the first pulse train ("Pulse train 1"), which are marked by crosses (+), and a second series of detection signal components obtained in response to the second pulse train ("Pulse train 2"), which are marked by dots.

Because of the different repetition rates, the discrete frequencies of each series of the detection signal components are spaced from each other by frequency spacings, which are different for the at least two series. In present example, the distance between two neighboring detection signal components (marked with "+") of the first series of detection signal components corresponds to a first repetition rate of the pulses of the first train of pulses of electromagnetic energy at a first wavelength, and the distance between two neighboring detection signal components (marked with dots) of the second series of detection signal components corresponds to a second repetition rate of the pulses of the second train of pulses of electromagnetic energy at a second wavelength.

Thus, the different responses of the target 5 to electromagnetic energy at different wavelengths (e.g. at the first and second wavelength in present example) is contained in the very same and/or single frequency spectrum and can be easily separated, e.g. by filtering out and/or selecting the first or second series of components, and transferred back into time domain, as exemplarily shown by "Signal 1 extracted" for the first series of detection signal components, and by "Signal 2 extracted" for the second series of detection signal components. These signals may be further evaluated, e.g. in order to derive a wavelength-dependent property, e.g. optical absorption, of the target 5.

The invention claimed is:

1. A device for optoacoustic sensing, in particular optoacoustic imaging, the device comprising:
an irradiation unit configured to generate at least one train of periodic pulses of electromagnetic energy, the pulses of the at least one train of periodic pulses exhibiting a pulse duration ($t_p$) and repetition rate (r) and the at least one train of periodic pulses exhibiting a train duration, and to irradiate a target with the generated at least one train of periodic pulses, a detection unit configured to detect acoustic waves generated in the target in response to irradiating the target with the at least one train of periodic pulses and to generate an according detection signal, the detection signal comprising, in particular for each train of the at least one train of periodic pulses, detection signal components at least three discrete frequencies in the frequency domain, the at least three discrete frequencies being spaced from each other by a frequency spacing corresponding to the repetition rate (r) of the pulses of the at least one train of periodic pulses, and a processing unit configured
to modify the detection signal in the frequency domain by filtering the detection signal in the frequency domain to obtain a modified detection signal, wherein filtering the detection signal in the frequency domain comprises filtering out signal components of the detection signal, in particular noise, at frequencies located between adjacent ones of the at least three discrete frequencies, while letting through signal components of the detection signal only at the at least three discrete frequencies, and
to derive at least one property of the target based on the modified detection signal;
wherein an inverse of a product of the repetition rate and the pulse duration of the pulses of the at least one train of periodic pulses of electromagnetic energy is at least 10, whereby the detection signal comprises discrete detection signal components at least 10 discrete frequencies in the frequency domain.

2. The device according to claim 1, the at least three discrete frequencies being in a frequency range between a lowest frequency and a highest frequency, wherein the lowest frequency corresponds to the repetition rate (r) of the pulses and/or the highest frequency is proportional to the reciprocal value of the pulse duration ($1/t_p$).

3. The device according to claim 1, the total number of detection signal components at the at least three discrete frequencies contained in the detection signal corresponding to the inverse of the product of the repetition rate (r) and the pulse duration ($t_p$).

4. The device according to claim 1, the total number of pulses contained in the train of periodic pulses being between 5 and 10000, preferably between 10 and 7500, in particular between 50 and 5000.

5. The device according to claim 1,
the detection unit being configured to detect the acoustic waves in the time domain and to generate the according detection signal in the time domain, and
the processing unit being configured to transform the detection signal into a transformed detection signal in the frequency domain and to modify the transformed detection signal in the frequency domain to obtain the modified detection signal.

6. The device according to claim 1, the detection unit being configured to detect the acoustic waves in the frequency domain.

7. The device according to claim 1, the detection unit comprising at least one of the following:
a spectrum analyzer configured to measure the magnitude of the detection signal versus frequency,
a lock-in amplifier configured to detect signal components of the detection signal at the at least three discrete frequencies, and
an I/Q demodulator configured to detect amplitude and phase of the signal components of the detection signal at the at least three discrete frequencies.

8. The device according to claim 1, wherein at least one of the following applies:
the pulse duration ($t_p$) of the pulses is between 0.5 ns and 100 ns, in particular between 1 ns and 10 ns,
the repetition rate (r) of the pulses is between 1 MHz and 200 MHz, in particular between 10 MHz and 100 MHz, and
the train duration of the train of periodic pulses is between 3 ps and 300 ms, in particular between 50 µs and 10 ms.

9. The device according to claim 1, the detection unit exhibiting a sensitivity field corresponding to an area or volume in which the detection unit is sensitive to acoustic waves, and the irradiation unit being configured to focus the electromagnetic energy on a focus area or volume on or in the target, wherein the sensitivity field of the detection unit is smaller than and/or located within the focus area or volume.

10. The device according to according to claim 1, the irradiation unit comprising a laser diode (LD) configured to continuously emit electromagnetic energy at a predetermined power level, and a laser diode driver configured to drive the laser diode to emit a train of periodic pulses of electromagnetic energy for irradiating the target, preferably at a power level above the predetermined power level.

11. The device according to claim 10, the laser diode driver comprising a capacitor electrically connected to the laser diode via a resistor, a voltage supply configured to charge the capacitor, and a power switch configured to close a current loop comprising the capacitor and the laser diode.

12. The device according to claim 1,
the irradiation unit being configured to generate at least two trains of periodic pulses of electromagnetic energy at different electromagnetic wavelengths, the pulses of the at least two trains of periodic pulses exhibiting different repetition rates (r), and to, in particular simultaneously, irradiate the target with the at least two trains of periodic pulses,
the detection unit being configured to detect acoustic waves generated in the target in response to irradiating the target with the at least two trains of periodic pulses and to generate an according detection signal comprising at least two series of detection signal components at a plurality of discrete frequencies in the frequency domain, wherein the discrete frequencies of each series of detection signal components are spaced from each other by a frequency spacing which corresponds to the repetition rate (r) of the pulses of the respective train of periodic pulses and is, therefore, different for each series, and
the processing unit being configured to modify the detection signal in the frequency domain, in particular to modify at least one of the series of the detection signal components at the plurality of discrete frequencies, to obtain a modified detection signal, and to derive the at least one property of the target based on the modified detection signal.

13. A method for optoacoustic sensing, in particular optoacoustic imaging, the method comprising the following steps:
- irradiating a target with at least one train of periodic pulses of electromagnetic energy, the pulses of the at least one train of periodic pulses exhibiting a pulse duration ($t_p$) and repetition rate (r) and the at least one train of periodic pulses exhibiting a train duration,
- detecting acoustic waves generated in the target in response to irradiating the target with the at least one train of periodic pulses and generating an according detection signal, the detection signal comprising, in particular for each train of the at least one train of periodic pulses, detection signal components at least three discrete frequencies in the frequency domain, the at least three discrete frequencies being spaced from each other by a frequency spacing corresponding to the repetition rate (r) of the pulses of the at least one train of periodic pulses,
- modifying the detection signal in the frequency domain to obtain a modified detection signal by filtering out signal components of the detection signal, in particular noise, at frequencies located between the at least three plurality of discrete frequencies, while letting through signal components of the detection signal only at the at least three discrete frequencies, and
- deriving at least one property of the target based on the modified detection signal;

wherein an inverse of a product of the repetition rate and the pulse duration of the pulses of the at least one train of periodic pulses of electromagnetic energy is at least 10, whereby the detection signal comprises discrete detection signal components at at least 10 discrete frequencies in the frequency domain.

14. The device according to claim 1, comprising a control unit configured to calculate the at least three discrete frequencies of the detection signal components based on the repetition rate and/or the pulse duration of the pulses, and to transmit said calculated at least three discrete frequencies of the detection signal components to the processing unit, based on which the filtering is performed.

15. The device according to claim 1, wherein the processing unit is configured to filter the detection signal in the frequency domain by applying a filter function to the detection signal, wherein the filter function is configured to pass peaks in the detection signal at the at least three discrete frequencies and to reject all other components of the detection signal.

16. The device according to claim 1, wherein the pulse duration ($t_p$) of the pulses is predetermined.

17. The device according to claim 1, wherein the repetition rate (r) of the pulses is predetermined.

18. The device according to claim 1, wherein the train duration of the at least one train of periodic pulses is predetermined.

* * * * *

UNITED STATES PATENT AND TRADEMARK OFFICE
CERTIFICATE OF CORRECTION

PATENT NO. : 12,064,212 B2
APPLICATION NO. : 16/629490
DATED : August 20, 2024
INVENTOR(S) : Ludwig Prade and Vasilis Ntziachristos Page 1 of 1

It is certified that error appears in the above-identified patent and that said Letters Patent is hereby corrected as shown below:

In the Claims

Claim 1, Column 17, Line 16 reads "...detection signal components at least three discrete frequencies in the frequency domain" which should read "...detection signal components at at least three discrete frequencies in the frequency domain..."

Claim 1, Column 17, Line 38 reads "...whereby the detection signal comprises discrete detection signal components at least 10 discrete frequencies in the frequency domain." which should read "...whereby the detection signal comprises discrete detection signal components at at least 10 discrete frequencies in the frequency domain..."

Claim 13, Column 19, Line 14 reads "detection signal components at least three discrete frequencies in the frequency domain" which should read "...detection signal components at at least three discrete frequencies in the frequency domain..."

Signed and Sealed this
Twenty-second Day of October, 2024

Katherine Kelly Vidal
*Director of the United States Patent and Trademark Office*